US006570043B2

(12) United States Patent
Elliott et al.

(10) Patent No.: US 6,570,043 B2
(45) Date of Patent: *May 27, 2003

(54) CONVERTING SUGARS TO SUGAR ALCOHOLS BY AQUEOUS PHASE CATALYTIC HYDROGENATION

(75) Inventors: Douglas C. Elliott, Richland, WA (US); Todd A. Werpy, West Richland, WA (US); Yong Wang, Richland, WA (US); John G. Frye, Jr., Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 28 days.

This patent is subject to a terminal disclaimer.

(21) Appl. No.: 09/845,646

(22) Filed: Apr. 27, 2001

(65) Prior Publication Data

US 2002/0133048 A1 Sep. 19, 2002

Related U.S. Application Data

(63) Continuation-in-part of application No. 09/389,389, filed on Sep. 3, 1999, now Pat. No. 6,235,797.

(51) Int. Cl.[7] .............................................. C07C 27/00
(52) U.S. Cl. ....................................... 568/863; 518/715
(58) Field of Search ........................... 568/863; 518/715

(56) References Cited

U.S. PATENT DOCUMENTS

| | | | | |
|---|---|---|---|---|
| 2,868,847 A | 1/1959 | Boyers | ........................ | 260/635 |
| 4,042,614 A | 8/1977 | Vannice et al. | ......... | 260/449 R |
| 4,503,274 A | 3/1983 | Arena | ........................ | 568/863 |
| 4,380,679 A | 4/1983 | Arena | ........................ | 568/863 |
| 4,380,680 A | 4/1983 | Arena | ........................ | 568/863 |
| 4,413,152 A | 11/1983 | Arena | ........................ | 568/863 |
| 4,487,980 A | 12/1984 | Arena | ........................ | 568/863 |
| 4,496,780 A | 1/1985 | Arena | ........................ | 568/861 |
| 4,510,339 A | 4/1985 | Arena | ........................ | 568/863 |
| 4,567,205 A | 1/1986 | Arcuri et al. | ............... | 518/715 |
| 5,616,154 A | 4/1997 | Elliott et al. | .............. | 48/197 R |
| 5,814,112 A | 9/1998 | Elliott et al. | .............. | 48/197 R |

FOREIGN PATENT DOCUMENTS

| | | | | |
|---|---|---|---|---|
| EP | 0741107 A2 | 11/1996 | ...................... | 3/38 |
| EP | 0936184 A2 | 8/1999 | ........................ | 7/4 |

OTHER PUBLICATIONS

"Low Temperature Catalytic Gasification Of Wet Industrial Wastes," FY 1991–1992 Interim Report, Elliot et al., pp. B–16, B–17 Jun. 1993.

"Low Temperature Catalytic Gasification Of Wet Industrial Wastes," FY 1991–1992 Interim Report, Elliot et al., pp. 23, 25, Mar. 1995.

"Glucose Hydrogenation on Ruthenium Catalysts in Trickle Bed Reactor," Gallezot et. al., Journal of Catalysis 180, 51–55 (1998).

*Primary Examiner*—Elli Peselev
(74) *Attorney, Agent, or Firm*—Wells St. John P.S.

(57) ABSTRACT

The present invention provides a method of converting sugars to their corresponding sugar alcohols by catalytic hydrogenation in the aqueous phase. It has been found that surprisingly superior results can be obtained by utilizing a relatively low temperature (less than 120° C.), selected hydrogenation conditions, and a hydrothermally stable catalyst. These results include excellent sugar conversion to the desired sugar alcohol, in combination with long life under hydrothermal conditions.

26 Claims, No Drawings

CONVERTING SUGARS TO SUGAR ALCOHOLS BY AQUEOUS PHASE CATALYTIC HYDROGENATION

RELATED APPLICATIONS

This application is a continuation-in-part of U.S. patent application Ser. No. 09/389,389, filed Sep. 3, 1999, now U.S. Pat. No. 6,235,797 B1, which is incorporated herein as if reproduced in full below.

STATEMENT OF GOVERNMENT RIGHTS

This invention was made with Government support under contract DE-AC0676RLO 1830 awarded by the U.S. Department of Energy. The Government has certain rights in this invention.

FIELD OF THE INVENTION

The present invention relates to methods of converting sugars to sugar alcohols using aqueous phase catalytic hydrogenation.

BACKGROUND OF THE INVENTION

Conventional heterogeneous catalysis has usually involved petroleum processing; however, in recent years there has been an increased emphasis on aqueous systems. As opposed to petroleum- or hydrocarbon-based systems, water-based systems have less toxicity and fewer environmental problems. Additionally, aqueous systems are well-suited for biologically-produced feedstocks. For example, sugars from biological sources can be extracted with or produced in water. Then, to prepare sugar alcohols from these sugar solutions, it is economically necessary to conduct catalytic hydrogenation in the aqueous phase.

For the commercially important glucose to sorbitol hydrogenation, Gallezot et al. remarked that the challenge was to obtain a high conversion of glucose with a high selectivity to sorbitol and "a high stability of the catalyst during a long period of time." See Gallezot et al., "Glucose Hydrogenation on Ruthenium Catalysts in a Trickle-Bed Reactor." However, despite the work of Gallezot et al. and others, there remains a need for improved methods of aqueous phase hydrogenation of sugars to sugar alcohols.

SUMMARY OF THE INVENTION

In a first aspect, the invention provides a method of converting sugar to sugar alcohol by catalytic hydrogenation in the aqueous phase. In this method, an aqueous sugar solution is passed into a reaction chamber. Temperature of solution in the reaction chamber is maintained at less than 120° C., and pressure in the reaction chamber is maintained at 100 to 3000 pounds per square inch gauge hydrogen gas overpressure. The reaction chamber contains a hydrothermally stable catalyst and, in the reaction chamber, the sugar reacts with hydrogen to produce a sugar alcohol. The reaction conditions are such that, when measured after 300 hours at the same reaction conditions, at least 97% of the sugar is converted to a sugar alcohol. Of course, each sugar is converted to its corresponding sugar alcohol, e.g. glucose to sorbitol, lactose to lactitol, etc. That the conversion of sugar to sugar alcohol is measured at 300 hours means that to test satisfactory reaction conditions (including selection of catalyst), a measurement is made after continuing to run 300 hours of operation at the same conditions without intervening steps of reactivating or replacing the catalyst; it does not mean that the invention is limited to reactions run for 300 hours or more.

In a second aspect, the invention provides a method of converting sugars to sugar alcohols by passing an aqueous sugar solution over a catalyst comprising ruthenium on a titania support, where the titania in the support is 75% or more in the rutile phase as measured by x-ray diffraction.

DESCRIPTION OF THE PREFERRED EMBODIMENT(S)

The aqueous sugar solutions used in the inventive methods contain at least one sugar dissolved in water. The sugar to be converted is preferably a mono—or disaccharide. Examples of preferred sugars that are hydrogenated in the present invention include: glucose, lactose, lactulose, fructose, erythrose, arabinose, mannose, xylose, galactose, and talose.

The aqueous sugar solutions are usually derived from biological sources, typically plants such as corn. The invention is defined in terms of converting a single type of sugar; however, the aqueous solutions may contain a mixture of sugars. Preferably, the sugar feedstocks are obtained pure or are purified prior to use in the reactor—impure feedstocks (often containing sulfur-containing species) may poison the catalyst, and thus require more frequent catalyst regeneration steps. Preferably, the sugar solutions are more than 99% by weight, more preferably 99.9%, water and sugar. Preferably the sugar is a single type of sugar such as glucose, arabinose, etc.

The sugar solutions are preferably 1 to 70 weight % sugar, more preferably 7 to 45 weight % sugar. The aqueous sugar solutions are preferably fed into the reaction chamber at fast rates, preferably fed into the reaction chamber at a rate of at least 0.5 kg sugar per liter of catalyst bed per hour, more preferably 0.9 kg sugar per liter of catalyst bed per hour, and still more preferably a rate of 1.2 kg/L/hr to 1.9 kg/L/hr.

Temperature in the reaction chamber is preferably maintained below 120° C. Higher temperatures require too much energy and can result in poorer selectivities and can cause faster catalyst degradation. More preferably, the temperature is maintained in a range of 90 to 120° C. Temperature is measured by placing a thermocouple in (or on) a catalyst bed in the reaction chamber. Pressure in the reaction chamber is preferably maintained in the range of 100 to 3000, more preferably 250 to 1900 pounds per square inch gauge. Pressure is generated by the hydrothermal conditions and is maintained in a desired range by hydrogen gas overpressure.

The hydrogenation catalyst must be an active hydrogenation catalyst and must also be stable in hydrothermal conditions. It has been discovered that a Ru on rutile catalyst exhibits exceptional properties for the aqueous phase hydrogenation of sugars to their corresponding sugar alcohols. It is believed that additional catalysts might be developed by routine testing utilizing the conditions and results described herein. Use of impure feed can poison the catalyst leading to loss of activity; the catalyst can be regenerated either by discontinuing reaction and hydrogen treatment or by switching to a purer feed solution.

Preferably, the catalyst that has an active metal on a titania support. The active metal preferably includes ruthenium and the titania is at least 75% rutile as measured by x-ray diffraction. Additionally, the catalyst is preferably essentially nickel-free and/or rhenium-free. It is desirable that catalyst metal be distributed over the surface of a support in a manner that maximizes surface area of the ruthenium. The metal preferably constitutes 0.1 to 10 weight % of the catalyst. Amounts of ruthenium above this range may not increase the catalyst's activity, while amounts below this range can have undesirably low processing rates. More preferably, ruthenium constitutes 1 to 5 weight % of the catalyst, and still more preferably 2 to 3 weight %. In a preferred embodiment, the active metal consists essentially of pure ruthenium. The ruthenium preferably constitutes at least 95 weight percent of the active metal, more preferably more than 98%, and still more preferably more than 99.8%.

The catalyst is preferably essentially without nickel, that is, nickel does not make a significant contribution to the catalytic activity of the catalyst. Nickel is prone to dissolution in the aqueous phase processing conditions and may contaminate the product. This is especially a problem where a food-grade product is desired, for example in hydrogenating carbohydrates. Moreover, nickel in the product stream can also present a problem with waste disposal. Additive metals such as nickel can also present complications when disposing or recovering catalyst. Preferably, the catalyst contains less than 0.1 weight % nickel, more preferably, less than 0.01 weight %.

Rhenium is another metal that can present the problems discussed above for nickel. The catalyst is preferably essentially without rhenium. This means that the rhenium to ruthenium ratio in the catalyst is less than 1:20 by weight. Preferably, rhenium, if present at all, is present in less than 0.005 weight % of the catalyst. Similarly, the catalyst is preferably essentially without cobalt.

The metal, preferably ruthenium, is preferably disposed on a titania support. For optimum activity, the metal should exist in small particles on the surface of the support. The surface of the support typically includes not only the exterior surfaces but also interior surfaces of a porous support. The support may be in a variety of forms such as powder, pellets, honeycomb, etc. The titania is preferably composed of at least 75% rutile, more preferably at least 90% rutile, and still more preferably at least 95% rutile. For purposes of the present invention, the % rutile is measured as follows. A powdered sample of the support (or catalyst) is analyzed by x-ray diffraction using a copper x-ray source operating at 45 kV and 40 mA scanning over the range of 5 to 75 2-theta degrees. The rutile and anatase phases can be identified by comparison with the JCPDS database reference patterns. The peak height of the largest rutile peak and largest anatase peak are used for quantitation. The % rutile is determined as a percentage of its peak height divided by the sum of the heights of the largest rutile and largest anatase peaks.

Hydrogenation reactions are best controlled by using a pure titania support. The support is preferably at least 90 weight % titania, more preferably at least 99.5% titania. Because binders, such as clays, may dissolve or interfere with catalytic activity, the support preferably does not contain binders. The catalyst can also be characterized by elemental analysis; preferably the catalyst comprises 54 to 60 weight % titanium, and 36 to 40 weight % oxygen.

Although it is possible to generate a rutile support in situ by selection of processing conditions that favor the formation of rutile, better and more consistent activity and stability can be achieved by using a support with a high level of rutile (at least 75%, more preferably 90%, and still more preferably 95%) prior to depositing ruthenium on the support's surface. Titania supports having a high level of rutile phase can be purchased or prepared. A suitable support is P25 code 7709 titania, available from Degussa Corporation, Parsippany, N.J., USA. This support can be used without additional calcination or thermal processing. Alternatively, titania can be prepared by known methods such as oxidation of titanium, water treatment of titanium chloride, and hydrolysis of titanium alkoxides. The support can be titania powder, but is preferably in the form of tablets, pellets, extrudates or other forms for use in a fixed bed catalyst system.

Ruthenium can be coprecipitated with titania, but for greater activity and economy it is preferably deposited onto the titania support. The ruthenium can be deposited onto a titania support by impregnating with aqueous ruthenium compositions such as aqueous ruthenium chloride. Other methods such as vapor deposition are also possible. After impregnation, water is removed by heating and the precipitated ruthenium compound reduced to the metal by reduction with hydrogen at elevated temperature. The reduction is preferably conducted at below 300° C., since reductions above this temperature have been shown to reduce the titania resulting in migration of the titanium to the ruthenium causing less of the ruthenium surface to be exposed, and loss of catalytic activity.

The inventive method is not limited to particular reactor types, and may generally be conducted in continuous stirred tank reactor (CSTR), fixed bed, fluidized bed, expanded bed, etc. The reaction chamber is where the catalyst is situated and where the hydrogenation reaction occurs. In the present invention, the term "reaction chamber" refers to the portion of the reaction chamber that is maintained at the reaction conditions. The volume of catalyst is defined based on the volume measured in the determination of the apparent bulk density of the catalyst, that is, as settle catalyst particles.

The amount of sugar converted to sugar alcohol is a function of sugar conversion and product selectivity. Preferably, the reaction converts at least 95% of the sugar in the feed stream, more preferably at least 97% and still more preferably at least 99%. Selectivity to the corresponding sugar alcohol, and percent of sugar converted to sugar alcohol, are each at least 95% more preferably at least 97% and still more preferably at least 99%. While measurements by liquid chromatography can be quite accurate (especially when averaged), gas chromatography is selected as the technique to measure the inventive methods, where nonvolatile components are derivatized prior to injection into the gas chromatograph.

One advantage of the inventive method is the capability to run the hydrogenation reaction over extended periods of time without regenerating the catalyst, and while maintaining excellent conversion and selectivity. The stability of the invention is measured by allowing the reaction to proceed for at least 300 hours, without regenerating the catalyst, and measuring the concentrations of sugar and sugar alcohol in the product stream. While the invention is measured according to this procedure, the inventive methods include production runs for less than and more than 300 hours. Preferably the reaction is conducted for at least 200 hours, more preferably at least 300 hours, and still more preferably at least 400 hours without regenerating the catalyst.

Another advantage of preferred embodiments of the invention is the extremely low levels of metal contamination in the product stream. Preferably the level of metals in the product stream is less than 15 parts per billion (ppb) in total metals (testing for metals present in the catalyst), more preferably less than 8 ppb.

EXAMPLES

The inventive process can be accomplished at low processing temperature while maintaining high processing rates. Even after long processing times, high conversion and good product selectivity are obtained. For example, some typical processing conditions and results are presented below. Some comparative testing versus conventional nickel catalyzed processes are also provided.

Example 1

A ruthenium on rutile titania extrudate catalyst obtained from Degussa (H7709 X/D 3% Ru) has been tested in the microhydrotreater reactor in continuous-flow hydrogenation of reagent grade glucose over a range of parameters. The initial tests with glucose, wherein some of the parameter conditions were tested, were part of an extended test including processing periods with lactose, lactitol, and sorbitol. Catalyst degradation through these 100+hours of tests was judged to be inconsequential (based on results with lactose). Conversion, yield and selectivity were measured separately using liquid chromatography resulting in some variation between yield and selectivity, probably as a result of inconsistent calibration.

| Glucose Hydrogenation Results - Continuous Reactor Tests | | | | | | | | | |
|---|---|---|---|---|---|---|---|---|---|
| Temp. deg C | LHSV* L/L/hr | % Feed concentration | Time, hr(day) on stream | % Glucose Conversion | Sorbitol yield, % | Selectivity % | C Gas yield, % | Polyol yield, % | $H_2$/feed mole ratio |
| 100 | 2 | 19.9 | 103 (19) | 100 | 94 | 96.7 | 0.18 | 0.31 | 7.2 |
| 100 | 4 | 19.9 | 105 (19) | 100 | 96.7 | 98.2 | 0.16 | 0 | 6.2 |
| 100 | 2 | 39.8 | 108 (20) | 99.98 | 95.5 | 96.4 | 0.21 | 0.43 | 3.4 |
| 100 | 4 | 39.8 | 109 (20) | 98.55 | 95.3 | 98.2 | 0.2 | 0.17 | 3.0 |
| 100 | 4 | 39.8 | 112 (20) | 98.02 | 94.8 | 98.2 | 0.18 | 0.2 | 5.9 |
| 100 | 6 | 19.9 | 114 (21) | 99.95 | 99.8 | 98.7 | 0.14 | 0 | 8.4 |

All tests at 1900 psig (13.2 MPa)
*equivalent to 0.9 to 1.9 kg sugar/L catalyst bed/hr These results show a highly active catalyst with high conversion and yield even with high concentration of feedstock and high liquid hourly space velocities. A slight feedstock concentration effect and processing rate effect are evident in the data given above. Selectivity of sorbitol (vs mannitol or other polyols) is very high in all tests but a slight trend to higher selectivity at higher processing rate is evident. Similarly, the C gas yield (methane primarily with a trace of carbon dioxide detectable at times) is very low in all tests but shows a slight trend to less gas production at higher processing rate, as well as at lower feedstock concentration. The hydrogen to glucose molar feed ratio had little effect with the range tested here. The comparison at 4 LHSV seemed to show a reduced reactivity (lower conversion, yields) at the higher gas flow rate.

A second series of tests was performed with a new catalyst test bed in the same reactor and the same catalyst lot. Only glucose was processed in this series. Higher processing rates were used with the two concentrations of glucose in water. The results in the table below show that the operating pressure has a strong effect on the reactivity of the system. As pressure is reduced the glucose conversion drops. Compare the third and fourth results with earlier results at 13.2 MPa and 8.4 mole feed ratio wherein there was 99.95% conversion, 99.8% sorbitol yield, and a gas yield of 0.14%. Or compare the first two results with 40% feedstock with earlier results of 98% conversion (@5.9 mole ratio and 13.2 MPA) and 95% sorbitol yield with a gas yield of 0.18%. The effect of relative flow of hydrogen appears to be a higher reactivity with higher hydrogen flow as evidenced by the higher conversion of glucose and higher gas yields. These tests show that the catalyst can be forced into an overload condition by too little hydrogen available for the reaction and too little time at reaction conditions.

Glucose Continuous Flow Processing Results

| Pressure Mpa | H₂/glucose mole ratio | LHSV L/L/hr | % Glucose Conversion | Sorbitol yield, % | Selectivity % | Polyol yield, % | Gas Yield, % | Hours on-stream |
|---|---|---|---|---|---|---|---|---|
| 10.3 | 4.1 | 6.0 | 89.7 | 79.2 | 100.0% | 0.0 | 0.21 | 1.2 |
| 10.3 | 4.1 | 6.0 | 87.8 | 74.4 | 98.9% | 0.0 | 0.21 | 2.0 |
| 10.3 | 7.8 | 6.0 | 96.2 | 85.8 | 100.0% | 0.0 | 0.24 | 3.4 |
| 10.3 | 7.8 | 6.1 | 96.1 | 81.6 | 100.0% | 0.0 | 0.23 | 4.9 |
| 6.9 | 4.1 | 6.0 | 90.1 | 84.2 | 98.5% | 0.0 | 0.21 | 6.0 |
| 6.9 | 7.8 | 6.0 | 91.4 | 82.3 | 98.6% | 0.0 | 0.24 | 8.3 |
| 3.4 | 4.1 | 6.0 | 73.3 | 70.7 | 94.4% | 3.0 | 0.28 | 11.6 |
| 1.7 | 4.0 | 6.1 | 55.0 | 41.8 | 100.0% | 0.0 | 0.12 | 14.4 |
| 1.7 | 4.1 | 6.0 | 56.2 | 46.1 | 98.9% | 0.0 | 0.53 | 15.1 |
| 1.7 | 12.5 | 2.0 | 91.1 | 93.8 | 96.6% | 0.0 | 0.79 | 16.6 |
| 3.4 | 7.8 | 6.0 | 75.1 | 81.2 | 98.7% | 0.0 | 0.25 | 18.4 |
| 10.3 | 5.6 | 4.0 | 38.2 | 37.1 | 100.0% | 0.0 | 0.09 | 20.8 |
| 10.3 | 5.6 | 4.0 | 39.3 | 35.2 | 100.0% | 0.0 | 0.09 | 21.6 |
| 10.3 | 2.9 | 4.0 | 40.2 | 37.4 | 100.0% | 0.0 | 0.08 | 22.6 |
| 10.3 | 2.8 | 4.0 | 47.0 | 43.5 | 100.0% | 0.0 | 0.09 | 23.3 |
| 6.9 | 2.8 | 4.0 | 33.0 | 31.4 | 100.0% | 0.0 | 0.08 | 25.5 |
| 6.9 | 2.8 | 4.0 | 36.1 | 29.1 | 100.0% | 0.0 | 0.08 | 26.0 |
| 6.9 | 5.6 | 4.0 | 39.2 | 37.1 | 100.0% | 0.0 | 0.09 | 27.3 |
| 6.9 | 5.6 | 4.0 | 36.2 | 36.0 | 100.0% | 0.0 | 0.09 | 27.8 |
| 3.4 | 2.9 | 4.0 | 23.1 | 20.7 | 100.0% | 0.0 | 0.08 | 29.0 |
| 3.4 | 2.8 | 4.0 | 23.1 | 21.2 | 100.0% | 0.0 | 0.09 | 29.8 |
| 3.4 | 5.4 | 4.1 | 32.1 | 20.9 | 100.0% | 0.0 | 0.17 | 31.8 |
| 3.4 | 5.4 | 4.1 | 31.9 | 20.8 | 100.0% | 0.0 | 0.17 | 33.0 |
| 1.7 | 2.8 | 4.0 | 21.0 | 14.9 | 100.0% | 0.0 | 0.09 | 34.6 |
| 1.7 | 2.8 | 4.0 | 20.7 | 14.9 | 100.0% | 0.0 | 0.09 | 35.2 |
| 1.7 | 5.5 | 4.0 | 27.4 | 17.5 | 100.0% | 0.0 | 0.09 | 37.4 |

All tests at 100 degrees Celsius feeding 20% (above double line) or 40 wt % glucose in DI water

Example 2

Additional tests were performed to show the effect of operating pressure and processing rate with a 40% feedstock. These results suggest that the glucose hydrogenation process can be operated at 1200 psig (8.3 MPa) and 100° C. with the 40% feedstock and achieve a 99.8% conversion at a 2.5 LHSV with closer to 100% conversion at a 2 LHSV (0.9 kg sugar/L catalyst bed/hr). The selectivity for sorbitol should be about 96% (at the lower conversion) with only a 0.2% loss of carbon to gas byproducts.

Glucose Comtinuous Flow Processing Results

| On stream hours | LHSV L/L/hr | pressure psig | temperature deg Celsius | % Glucose conversion | Sorbitol yield, % | Selectivity % | Gas yield, % |
|---|---|---|---|---|---|---|---|
| 17.8 | 2 | 1890 | 100.2 | >99.996 | 94.2% | 93.4% | 0.09% |
| 26.1 | 2 | 1500 | 100.5 | 100.0% | 92.8% | 94.1% | 0.21% |
| 42.2 | 2 | 980 | 100.5 | 100.0% | 93.2% | 94.0% | 0.24% |
| 49.9 | 2 | 490 | 101.4 | 99.4% | 96.0% | 96.0% | 0.29% |
| 64.2 | 2 | 255 | 101.4 | 81.5% | 89.2% | 96.5% | 0.22% |
| 67.2 | 2 | 1900 | 100 | 99.7% | 95.0% | 92.5% | NA |
| 72.3 | 3 | 1900 | 101 | 99.9% | 95.2% | 95.2% | NA |
| 88.7 | 3 | 1500 | 101 | 99.8% | 97.0% | 95.9% | 0.19% |
| 95.7 | 3 | 1020 | 101.1 | 98.6% | 102.0% | 96.7% | 0.16% |
| 121.0 | 2.5 | 1160 | 100.4 | 99.8% | 99.8% | 95.4% | NA |
| 148.5 | 2.5 | 1190 | 100.4 | 99.8% | 101.4% | 95.9% | 0.21% |

All tests feeding 40 wt % glucose in DI water with 3.7 mole H₂ per mole glucose

Example 3

The ruthenium on rutile titania extrudate catalyst from Degussa (H7709 X/D 3% Ru) was tested in the microhydrotreater reactor in continuous-flow hydrogenation of several grades of dextrose (commercial d-glucose) over a range of parameters. The dextrose products were received from Archer Daniels Midland (ADM) as concentrates from corn wet milling and were diluted to 40% glucose with water purified by reverse osmosis (RO) prior to processing.

Table 1 below shows results from the first test. It is divided into two parts: first the ADM feedstock ("defructosed" dextrose) was processed for over two hundred hours, then reagent glucose was processed. An initial loss of activity is evident in the first 46 hours of processing the ADM feed. The processing rate was reduced, which resulted in some recovery of conversion, but the loss of activity continued over the next 5 days. At that point the activity drop may have been leveling off. The temperature was increased, which resulted in recovery of some activity. But over the last day the activity appeared to still be dropping slightly. As the feedstock was then exhausted reagent glucose was introduced (at the same processing conditions) and an immediate increase in activity was noted.

The catalyst activity did not recover to the expected level, however. Over the subsequent 3 days the activity dropped only slightly.

The defructosed dextrose was determined to be ~98% glucose with residual maltose, maltotriose and higher carbohydrates (0.2% fructose). It contained significant levels of sulfur and phosphorus, 3 ppm and 28 ppm, respectively by inductively coupled plasma spectrophotometry (ICP), with the sulfur confirmed as 23 ppm sulfate by ion chromatography IC (chloride at 4 ppm). The products at 21 hr and 161 hr on stream were similar in that each contained about 12–13 ppm sulfate and 2–3 ppm chloride. Similarly, the ICP results showed that the sulfur content of the products dropped to about one half of that in the feedstock. Sodium, calcium and phosphorus levels in the feedstock also dropped by half in the processing suggesting that they were deposited on the catalyst. A product sample from the later, higher temperature operations showed no significant difference in the trace element contents of the feed compared to the product. No ruthenium (<0.01 ppm) from the catalyst was detected in any of the product liquids. Iron from the reactor walls was noticeable in trace amounts (<1 ppm) in the products.

| On stream hours | LHSV L/L/hr | pressure psig | temperature deg Celsius | % Glucose conversion | Sorbitol yield, % | Selectivity % | Gas yield, % |
|---|---|---|---|---|---|---|---|
| initial glucose feed ~98% purity | | | | | | | |
| 21.4 | 2.5 | 1180 | 102 | 90.38% | 97.40% | 94.6% | 0.22% |
| 40 | 2.5 | 1180 | 102 | 85.72% | 92.49% | 95.1% | 0.19% |
| 46.3 | 2.5 | 1180 | 102 | 83.93% | 89.88% | 95.5% | NA |
| 78.3 | 2 | 1160 | 102 | 87.49% | 91.91% | 95.5% | 0.19% |
| 119.2 | 2 | 1190 | 101 | 83.82% | 91.91% | 96.0% | 0.16% |
| 133.7 | 2 | 1200 | 102 | 81.24% | 88.44% | 96.1% | 0.16% |
| 139.4 | 2 | 1200 | 102 | 77.57% | 86.71% | 95.0% | NA |
| 153.5 | 2 | 1200 | 99 | 73.61% | 81.50% | 94.8% | 0.15% |
| 160.9 | 2 | 1210 | 99.2 | 72.80% | 78.32% | 97.1% | 0.14% |
| 176.8 | 2 | 1200 | 118.1 | 88.55% | 90.75% | 89.7% | 0.35% |
| 184.2 | 2 | 1200 | 118 | 88.53% | 93.06% | 90.8% | 0.36% |
| 208.3 | 2 | 1200 | 117.7 | 88.12% | 91.91% | 90.9% | 0.30% |
| Glucose 2 40% reagent feedstock | | | | | | | |
| 229.7 | 2 | 1210 | 118.4 | 98.58% | 94.75% | 92.8% | 0.33% |
| 272 | 2 | 1230 | 118.7 | 98.50% | 93.75% | 92.8% | 0.33% |
| 280 | 2 | 1230 | 118.8 | 98.43% | 98.00% | 92.4% | 0.32% |
| 295.5 | 2 | 1230 | 118.4 | 98.35% | 96.25% | 92.3% | 0.33% |

Example 4

A new bed of ruthenium on rutile catalyst was put into the reactor and the test was restarted with higher purity dextrose (99.5%). Initial processing at the 2.5 LHSV showed a steady drop in catalyst activity after the first day of startup operations. The loss of activity was tracked over a week of operation before the feedstock supply was exhausted. The conversion was still >97% after over 150 hours in operation.

| 99.5% detrose feedstock | | | | | | | |
|---|---|---|---|---|---|---|---|
| 2.28 | 2.5 | 1220 | 102.2 | 97.19% | 96.48% | 95.4% | NA |
| 4.06 | 2.5 | 1210 | 102.4 | 96.91% | 97.24% | 93.1% | 0.24% |
| 6.73 | 2.5 | 1190 | 101.8 | 99.35% | 91.96% | 90.0% | NA |
| 21.48 | 2.5 | 1190 | 102.3 | 99.70% | 96.98% | 91.2% | NA |
| 28.4 | 2.5 | 1200 | 100.7 | 99.65% | 101.76% | 94.2% | NA |
| 29.8 | 2.5 | 1200 | 100.7 | 99.52% | 104.27% | 94.7% | NA |
| 53.35 | 2.5 | 1150 | 100.7 | 99.07% | 98.49% | 95.2% | NA |
| 92.87 | 2.5 | 1210 | 100.6 | 98.09% | 102.26% | 96.5% | 0.18% |
| 116.29 | 2.5 | 1200 | 101.1 | 97.59% | 105.28% | 97.1% | 0.18% |
| 124.62 | 2.5 | 1210 | 101 | 97.44% | 101.51% | 97.2% | NA |
| 140.07 | 2.5 | 1210 | 100.8 | 96.86% | 99.50% | 97.3% | 0.17% |
| 148.69 | 2.5 | 1215 | 101 | 97.06% | 97.74% | 97.4% | 0.17% |
| 151.62 | 2.5 | — | — | 97.09% | 96.23% | 97.2% | NA |

Example 5

Reagent glucose was then introduced as the feedstock and the test was continued with the same catalyst bed. Activity with the reagent glucose was similar to the high-purity dextrose except that the trend in loss of activity ceased and operation was stable for a day. In an attempt to recover the high conversion, the processing rate was reduced to an LHSV of 2.2 (1.0 kg sugar/L catalyst bed/hr) and then 2.0 (0.9 kg sugar/Liter catalyst bed/hr). As expected the conversion increased with little loss of sorbitol product selectivity. During the five days of operation with the reagent glucose, there appeared to be no loss of catalyst activity.

| Glucose 3 40% reagent feedstock | | | | | | | |
|---|---|---|---|---|---|---|---|
| 165.2 | 2.5 | 1210 | 101 | 96.65% | 105.54% | 97.2% | NA |
| 172.65 | 2.5 | 1205 | 100.9 | 96.73% | 101.26% | 97.4% | 0.17% |
| 189.2 | 2.5 | 1215 | 100.9 | 97.03% | 103.27% | 97.4% | 0.19% |
| 191.62 | 2.5 | 1215 | 101 | 97.00% | 105.54% | 97.3% | 0.19% |
| 196.35 | 2.2 | 1230 | 100.7 | 98.51% | 106.80% | 96.6% | 0.20% |
| 220.87 | 2.2 | 1235 | 100.6 | 98.66% | 108.31% | 97.0% | 0.19% |
| 238.62 | 2.2 | 1230 | 100.7 | 98.64% | 106.80% | 96.2% | 0.20% |
| 260 | 2.2 | 1240 | 100.7 | 98.67% | 93.46% | 96.7% | NA |
| 269.1 | 2.2 | 1240 | 100.7 | 98.52% | 100.48% | 97.2% | 0.19% |
| 274.7 | 2 | 1230 | 100.5 | 99.25% | 101.45% | 96.8% | 0.23% |
| 280.7 | 2 | 1250 | 100 | 99.27% | 104.12% | 96.8% | NA |
| 284.5 | 2 | 1250 | 100.4 | 99.27% | 104.12% | 96.4% | NA |

Upon introduction of the next feedstock aliquot there was a dramatic loss of activity in the catalyst bed. This product was found to be contaminated, apparently with a much less well refined dextrose product. The test was terminated and the catalyst removed for analysis. The feed was found to carry a high level of trace elements: 63 ppm S, 26 ppm P, 45 ppm Na, 41 ppm K, 24 ppm Ca, 9 ppm Mg.

| partially refined dextrose | | | | | | | |
|---|---|---|---|---|---|---|---|
| 298.7 | 2 | — | 100.5 | 98.47% | 113.49% | 96.6% | NA |
| 302.3 | 2 | 1260 | 100.6 | 90.16% | 107.94% | 98.3% | NA |
| 308.1 | 2 | 1270 | 101.2 | 78.84% | 98.94% | 98.7% | NA |
| 333 | 2 | 1240 | 99.6 | 55.03% | 71.43% | 98.4% | |
| 341 | 2 | 1250 | 99.3 | NA | NA | NA | NA |

The catalyst was analyzed by ICP for elemental composition and by electron microscopic techniques. The ICP was difficult to quantify because of the nature of the catalyst and difficulties with dissolution; but elevated levels (as much as 1000 ppm) of S, P, Ca and Fe were believed found. Images from TEM showed a well-dispersed ruthenium on titania material. Titania crystallites appeared to be about 1000 angstroms with ruthenium particles in the range of 100 down to 10 angstroms. EDS analysis was used to confirm the composition of the particles found in the TEM image. In addition, the EDS showed no significant amount of any of the trace contaminants in the feedstock associated with the ruthenium or titania particles in the catalyst. Therefore, no conclusive findings could be made as to the cause of the catalyst deactivation, other than the minimal and inconsistent evidence for trace element deposition on the catalyst. However, it is clear that the catalyst deactivation is only minor and is not due to a significant change in the structure of the catalyst.

Example 6

A third catalyst bed was placed in the reactor and the testing restarted with a new shipment of 99.5% dextrose product, diluted to 40% with RO water. This test demonstrated the high activity and stability of the ruthenium on titania catalyst for glucose hydrogenation in the aqueous phase. High activity was evident from the start of the test. Following a breakin period, the percent selectivity for the sorbitol product was consistently in the high 90s. The process was run at a 2 LHSV with an operating pressure of 1200 psig and temperature of 100° C.

| 99.5% glucose feedstock | | | | | | | |
|---|---|---|---|---|---|---|---|
| 17.05 | 2 | 1180 | 102.7 | 99.71% | 87.47% | 87.1 | 0.33% |
| 19.3 | 2 | 1170 | 103 | 99.82% | 90.81% | 87.7 | NA |
| 41.1 | 2 | 1190 | 103.4 | 99.39% | 86.91% | 89.3 | 0.36% |
| 46.9 | 2 | 1190 | 103.4 | 99.82% | 93.59% | 90.4 | NA |
| 73.1 | 2 | 1205 | 103.6 | 99.59% | 89.69% | 91.8 | NA |
| 111.6 | 2 | 1160 | 103.9 | 99.64% | 94.01% | 93.0 | 0.28% |
| 121.1 | 2 | 1100 | 104 | 99.81% | 95.54% | 94.2 | NA |
| 136.4 | 2 | 1210 | 104 | 99.78% | 101.11% | 94.6 | 0.31% |
| 145.2 | 2 | 1160 | 101.1 | 99.30% | 105.85% | 93.7 | NA |
| 159.9 | 2 | 1210 | 101.1 | 99.68% | 104.83% | 95.0 | NA |
| 169.8 | 2 | 1100 | 101.3 | 99.30% | 101.07% | 96.1 | 0.13% |
| 183.9 | 2 | 1150 | 101.3 | 99.77% | 103.22% | 95.9 | 0.25% |
| 192.1 | 2 | 1000 | 101.4 | 99.71% | 105.36% | 96.2 | NA |
| 208 | 2 | 1235 | 101.5 | 99.75% | 103.49% | 96.3 | NA |
| 219.3 | 2 | 1220 | 101.7 | 99.75% | 101.88% | 96.6 | NA |
| 279.4 | 2 | 1220 | 101.5 | 99.69% | 98.12% | 96.8 | 0.18% |
| 286.9 | 2 | 1220 | 101.7 | 99.64% | 99.46% | 97.0 | NA |
| 304.4 | 2 | 1180 | 101.7 | 99.61% | 99.73% | 97.0 | 0.20% |
| 314.3 | 2 | 1220 | 101.8 | 99.61% | 98.40% | 97.1 | NA |
| 328.1 | 2 | 1220 | 101.6 | 99.50% | 101.60% | 97.1 | 0.17% |
| 351.8 | 2 | 1250 | 101.5 | 99.47% | 101.07% | 97.3 | 0.19% |

| -continued | | | | | | | |
|---|---|---|---|---|---|---|---|
| 99.5% glucose feedstock | | | | | | | |
| 361.8 | 2 | 1220 | 101.6 | 99.42% | 98.93% | 97.3% | NA |
| 374.8 | 2 | 1215 | 101.5 | 99.40% | 100.27% | 97.5% | 0.18% |
| 387.3 | 2 | 1225 | 101.5 | 99.25% | 98.40% | 97.3% | NA |
| 429.3 | 2 | 1250 | 101.4 | 99.12% | 91.71% | 97.5% | 0.19% |
| 470.5 | 2 | 1280 | 101.1 | 98.48% | 98.13% | 97.6% | 0.14% |
| 474.4 | 2 | 1260 | 101.1 | 98.11% | 93.85% | 97.8% | NA |
| 480 | 1.8 | 1280 | 101.1 | 98.67% | 99.73% | 97.5% | NA |
| 496.6 | 1.8 | 1200 | 101 | 98.20% | 98.66% | 97.6% | 0.20% |
| 503.2 | 1.8 | 1200 | 101 | 98.17% | 95.99% | 97.6% | NA |
| 518.9 | 1.8 | 1200 | 100.9 | 97.98% | 95.72% | 97.7% | 0.19% |
| 526.3 | 1.8 | 1200 | 101.1 | 97.59% | 97.59% | 97.7% | NA |
| 542.8 | 1.8 | 1200 | 101.8 | 97.22% | 92.25% | 97.7% | NA |
| 545.9 | 1.8 | 1200 | 102.1 | NA | NA | NA | 0.23% |
| 550.1 | 1.8 | 1200 | 102.1 | 98.22% | 94.92% | 97.6% | NA |
| 613.9 | 1.8 | 1230 | 102 | 97.34% | 94.12% | 97.6% | 0.18% |

After 2 weeks of operation (375 hr) a trend of decreasing conversion was observed. At the end of 3 weeks the processing rate was reduced to increase the conversion. After this tactic was proven for 2–3 days of operation, a second tactic was also tested. The catalyst bed was washed with hot (100° C.) water and then hot acid (glacial acetic). This tactic provided only minor relief and the test was terminated soon after.

Example 7

Comparative tests were performed in the semi-batch reactor system to evaluate a Ru-based catalyst system versus a more conventional nickel-based system. These tests show that ruthenium at only 3% metal loading has about the same activity as nickel at 50% metal loading. This comparison is only for short-term activity of the catalyst.

6 hr Batch Tests with 1500 psig $H_2$

50% Ni on $SiO_2$ was very active (99% conversion of lactose @1 hr) at 140° C. with 12% lactose in water, but reduced (65%) selectivity to lactitol (91% total alditols). At 100° C. with 12% concentration has 95% conversion @2 hr (99% @3 hr) with 86% selectivity to lactitol (98% alditols—counting dulcitol and lactulitol).

3% ruthenium on $TiO_2$ at 140° C. with 12% concentration of lactose in water also showed high conversion of lactose (95% @1 hr) with high selectivity to lactitol (85%, or 94% alditols). At 100° C. with 12% concentration the conversion was 97% @2 hr (99% @3 hr) with 98% selectivity to lactitol.

Example 8

A ruthenium on rutile titania extrudate catalyst from Degussa (H7709 X/D 3% Ru) was tested in the microhydrotreater reactor in continuous-flow hydrogenation of reagent grade lactose over a range of parameters. As demonstrated in the continuous flow tests below, the nickel catalyst losses activity readily in the first hours on stream while the ruthenium maintains its activity at a high level.

Lactose Hydrogenation Results - Continuous Reactor Tests

| catalyst | Temp. deg C. | LHSV L/L/hr | % Feed concentration | Time, hr (day) on stream | % lactose Conversion | lactitol yield, % | Selectivity % | C Gas yield, % | Polyol yield, % | H$_2$/feed mole ratio |
| --- | --- | --- | --- | --- | --- | --- | --- | --- | --- | --- |
| Ni/SiO | 140 | 2 | 11 | 2.5 (1) | 100 | 62 | 4.3 | 0.07 | 23 | 13.7 |
| Ni/SiO | 140 | 2 | 11 | 18 (3) | 100 | 97 | 128 | 0 | 0 | 13.7 |
| Ni/AlO | 140 | 2 | 11 | 18 (3) | 100 | 86 | 25 | 0 | 9.7 | 10.3 |
| Ru/TiO | 140 | 2 | 18.4 | 6 (1) | 100 | 23 | 0.8 | 2.6 | 35 | 12.6 |
| Ru/TiO | 140 | 12 | 18.4 | 40 (7) | 99.6 | 82 | 9 | 0.4 | 9.8 | 12.9 |
| Ru/TiO | 120 | 6 | 18.4 | 27 (4) | 99.8 | 93 | 26.3 | 0.14 | 4.1 | 12.6 |
| Ru/TiO | 100 | 2 | 18.4 | 48 (9) | 100 | 95 | 52 | 0.06 | 3.1 | 13.3 |
| Ru/TiO | 100 | 4 | 18.4 | 50 (9) | 99.2 | 98 | 112 | 0.05 | 1.6 | 13.1 |
| Ru/TiO | 120 | 6 | 18.4 | 76.5 (14) | 99.8 | 92.5 | 26.2 | 0.135 | 4.8 | 13.3 |

All tests at 1900 psig (13.2 Mpa)

These results showed a highly active Ni/SiO$_2$ catalyst which at the tested processing rate causes over-reaction of the lactose through lactitol to polyols and some gases. After a short period on line the nickel catalyst activity dropped to a lower level such that the reaction appeared to be finished for the most part at the preferred lactitol product. The Ni/Al$_2$O$_3$ catalyst has similar activity. The Ru/TiO$_2$ catalyst shows even higher activity with significant levels of over-reaction products at the same processing conditions. However, it also shows sustained activity such that it can be operated at much higher throughput and concentration of feedstock and still achieve nearly equivalent conversion and selectivity after a longer time on stream. The nickel catalysts have much lower activity after only one day on stream, so that the ruthenium can be operated at lower temperature, higher processing rate and higher feed concentration to achieve similar product distributions. The Ru/TiO$_2$ catalyst shows selectivity of lactitol (vs lactulitol or other polyols) at very high levels in tests at the highest processing rates and lowest temperature. Similarly, the C gas yield (methane primarily with a trace of carbon dioxide detectable at times) is very low in all tests but shows a trend to less gas production at higher processing rate. The stability of the Ru/TiO$_2$ catalyst is shown by the reproducibility of the test results at the same conditions (120° C. and 6 LHSV) early in the test at 27 hours on stream and at 76.5 hours.

Monitoring metal contamination in products from these tests showed that the dissolution of the Ru-based catalyst materials was low in all cases. The product samples ranged from 2 ppb Ru down to undetectable in the product solution and from 11 ppb Ti down to 0.1 ppb.

CLOSURE

While preferred embodiments of the present invention have been described, it will be apparent to those skilled in the art that many changes and modifications may be made without departing from the invention in its broader aspects. The appended claims are therefore intended to cover all such changes and modifications as fall within the true spirit and scope of the invention.

What is claimed:

1. A process of converting sugar to sugar alcohol by catalytic hydrogenation in the aqueous phase, comprising:
    passing an aqueous sugar solution into a reaction chamber at a rate of at least 0.5 kg sugar per liter of catalyst bed per hour;
    maintaining temperature of solution in the reaction chamber at less than 120° C.;
    maintaining pressure in the reaction chamber of 100 to 3000 pounds per square inch gauge hydrogen gas overpressure;
    reacting the sugar with hydrogen over a hydrothermally stable catalyst comprising ruthenium on a titania support, the catalyst being essentially without nickel and essentially without rhenium, the titania being at least 75% rutile phase titania; wherein, when measured after 300 hours at the same reaction conditions, at least 97% of the sugar is converted to a sugar alcohol.

2. The process of claim 1 wherein the sugar solution comprises a monosaccharide.

3. The process claim 1 wherein the sugar solution comprises a disaccharide.

4. The process of claim 1 wherein the sugar solution comprises a sugar selected from the group consisting of glucose, and lactose.

5. The process of claim 4 wherein the sugar solution comprises more than 99 weight % sugar and water.

6. The process of claim 1 wherein the sugar solution contains 1 to 70 weight % sugar.

7. The process of claim 4 wherein the sugar solution contains 7 to 45 weight % sugar.

8. The process of claim 1 wherein the temperature is in the range of 90 to 120° C.

9. The process of claim 1 wherein pressure in the reaction chamber is in the range of 250 to 1900 psig.

10. The process of claim 1 wherein the catalyst is regenerated by switching to a more pure aqueous sugar solution.

11. The process of claim 1 wherein the ruthenium constitutes 2 to 3 weight % of the catalyst.

12. The process of claim 1 wherein the catalyst support is at least 90 weight % titania.

13. The process of claim 1 wherein at least 99% of the sugar is converted to sugar alcohol, when measured after 300 hours at the same reaction conditions.

14. The process of claim 1 wherein a product stream is recovered from the reaction chamber, and said product stream contains less than 8 parts per billion of metal contamination.

15. The process of claim 1 wherein the aqueous sugar solution is passed into the reaction chamber at a rate of 0.5 to 1.9 kg sugar per liter of catalyst bed per hour.

16. The process of claim 12 wherein the aqueous sugar solution is passed into the reaction chamber at a rate of at least 0.9 kg sugar per liter of catalyst bed per hour.

17. A method of hydrogenating a sugar comprising:
    providing a catalyst within a reactor, the catalyst being essentially free of nickel and rhenium and comprising ruthenium and titania, the titania being at least 75% rutile titania;
    contacting the catalyst with a solution comprising at least one sugar; and in the presence of the catalyst, reacting the sugar with hydrogen to form a hydrogenated product comprising sugar alcohol.

18. The method of claim 17 wherein the active metal consists essentially of ruthenium.

19. The method of claim 17 wherein the catalyst is essentially free of cobalt.

20. The method of claim 17 wherein the solution comprises a sugar selected from the group consisting of glucose, lactose, lactulose, fructose, erythrose, arabinose, mannose, xylose, galactose and talose.

21. The method of claim 17 further comprising forming the catalyst, the forming comprising:

providing a support comprising titania; and depositing the active metal onto the titania.

22. The method of claim 21 wherein the titania is at least 75% rutile prior to depositing the active metal.

23. A method of producing a sugar alcohol comprising:

providing a reaction chamber containing a catalyst comprising ruthenium and a titania support, the titania being at least 75% rutile; the catalyst being essentially free of rhenium and nickel;

initiating a flow of a solution containing at least one sugar into the reaction chamber;

reacting the at least one sugar with hydrogen within the reactor in the presence of the catalyst to produce a product solution comprising sugar alcohol; and flowing the product solution from the reactor.

24. The method of claim 23 wherein the median chamber comprises a temperature of less than 120° C.

25. The method of claim 23 wherein the flow of solution comprises a flow of from about 0.5 to about 1.9 kg of the at least one sugar per liter of catalyst bed into the reaction chamber per hour, and wherein during an initial flow time of at least 150 hours at least 97% of the sugar in the solution is converted to sugar alcohol in an absence of any catalyst regeneration.

26. The method of claim 23 wherein the at least 150 hours is greater than or equal to 300 hours.

* * * * *

UNITED STATES PATENT AND TRADEMARK OFFICE
CERTIFICATE OF CORRECTION

PATENT NO.   : 6,570,043 B2
DATED        : May 27, 2003
INVENTOR(S)  : Douglas C. Elliott et al.

It is certified that error appears in the above-identified patent and that said Letters Patent is hereby corrected as shown below:

<u>Column 16,</u>
Line 9, replace "median" with -- reaction --.

Signed and Sealed this

Second Day of September, 2003

JAMES E. ROGAN
*Director of the United States Patent and Trademark Office*